(12) United States Patent
Luo et al.

(10) Patent No.: US 12,326,452 B1
(45) Date of Patent: Jun. 10, 2025

(54) PREPARATION METHOD AND APPLICATION OF NANOBODY TARGETING DENGUE VIRUS NS1 PROTEIN

(71) Applicant: NANJING UNIVERSITY, Jiangsu (CN)

(72) Inventors: Yi Luo, Jiangsu (CN); Shixiang Yang, Jiangsu (CN); Wenjin Hu, Jiangsu (CN); Xiaolong Wang, Jiangsu (CN); Shengyang Wang, Jiangsu (CN); Huai Lin, Jiangsu (CN); Xiang Long, Jiangsu (CN)

(73) Assignee: NANJING UNIVERSITY, Jiangsu (CN)

( * ) Notice: Subject to any disclaimer, the term of this patent is extended or adjusted under 35 U.S.C. 154(b) by 0 days.

(21) Appl. No.: 18/955,940

(22) Filed: Nov. 21, 2024

(30) Foreign Application Priority Data

Dec. 8, 2023 (CN) .......................... 202311678044.5

(51) Int. Cl.
*G01N 33/569* (2006.01)
*C07K 16/10* (2006.01)

(52) U.S. Cl.
CPC ... *G01N 33/56983* (2013.01); *C07K 16/1081* (2013.01); *C07K 2317/569* (2013.01); *C07K 2317/92* (2013.01); *G01N 2333/183* (2013.01)

(58) Field of Classification Search
CPC ....... G01N 33/56983; G01N 2333/183; C07K 16/1081; C07K 2317/569; C07K 2317/92
See application file for complete search history.

(56) References Cited

U.S. PATENT DOCUMENTS 11,873,348 B2 * 1/2024 Ellmark ................. C07K 16/32

FOREIGN PATENT DOCUMENTS

| CN | 106279410 | 1/2017 |
|----|-----------|--------|
| CN | 109320607 | 2/2019 |
| CN | 116478242 | 7/2023 |
| WO | 2020245663 | 12/2020 |
| WO | 2022192532 | 9/2022 |

OTHER PUBLICATIONS

Shriver-Lake LC, Liu JL, Zabetakis D, Sugiharto VA, Lee CR, Defang GN, Wu SL, Anderson GP, Goldman ER. Selection and Characterization of Anti-Dengue NS1 Single Domain Antibodies. Sci Rep. Dec. 27, 2018;8(1):18086. (Year: 2018).*
Deschaght et al (2017). Large Diversity of Functional Nanobodies from a Camelid Immune Library Revealed by an Alternative Analysis of Next-Generation Sequencing Data. Front Immunol. 10;8:420. (Year: 2017).*
Pei-Yin Lim et al., "A nonstructural protein 1 capture enzymelinked immunosorbent assay specific for dengue viruses", PLOS ONE, May 18, 2023, pp. 1-15.
Xue; Zhi-Jing et al., "Research progress in molecular biological characteristics and detection methods of Dengue virus", Chin J Vector Biol & Control, Apr. 2019, with English abstract, pp. 224-227, vol. 30, No. 2.
Monica Poggianella et al., "Nanobodies Selectively Binding to the Idiotype of a Dengue Virus Neutralizing Antibody Do Not Necessarily Mimic the Viral Epitope", Biomolecules, Mar. 17, 2023, pp. 1-13.

* cited by examiner

*Primary Examiner* — Janet L Andres
*Assistant Examiner* — Samadhan Jaising Jadhao
(74) *Attorney, Agent, or Firm* — JCIPRNET

(57) ABSTRACT

Disclosed are a preparation method and application of a nanobody targeting dengue virus NS1 protein. The nanobody targeting dengue virus NS1 protein is a VHH antibody, which is obtained by constructing a nanobody phage library through phage screening technology, and has an amino acid sequence shown in SEQ ID NO: 1. The nanobody in the present disclosure exhibits high affinity and specificity when being bound to the dengue virus NS1 protein, and has advantages of good stability and low cost compared with monoclonal antibodies. Therefore, the nanobody in the present disclosure can be produced on a large scale, and has bright application prospects in the field of dengue virus detection and analysis.

3 Claims, 1 Drawing Sheet
Specification includes a Sequence Listing.

FIG. 1

SEQUENCE LISTING

```
Sequence total quantity: 2
SEQ ID NO: 1              moltype = AA   length = 124
FEATURE                   Location/Qualifiers
source                    1..124
                          mol_type = protein
                          organism = synthetic construct
SEQUENCE: 1
EVQVVESGGG LVQADSSLRL SCTASGRTFS SYAMGWFRQA PGKEREFVAR ISRSGRVTSY  60
ADSAKGRFTI SRDNAKNTLY LQMNSLHVED TAVYYCATRP LAAISRIRSD YDYWGQGTQV 120
TVSS                                                              124

SEQ ID NO: 2              moltype = DNA   length = 372
FEATURE                   Location/Qualifiers
source                    1..372
                          mol_type = other DNA
                          organism = synthetic construct
SEQUENCE: 2
gaagtgcagg tggtggaaag cggcggcggc ctggtgcagg cggatagcag cctgcgcctg  60
agctgcaccg cgagcggccg cacctttagc agctatgcga tgggctggtt tcgccaggcg 120
ccgggcaaag aacgcgaatt tgtggcgcgc attagccgca gcggccgcgt gaccagctat 180
gcggatagcg cgaaaggccg ctttaccatt agccgcgata cgcgaaaaaa cacctgtat 240
ctgcagatga acagcctgca tgtggaagat accgcggtgt attattgcgc gacccgcccg 300
ctggcggcga ttagccgcat tcgcagcgat tatgattatt ggggccaggg cacccaggtg 360
accgtgagca gc                                                     372
```

PREPARATION METHOD AND APPLICATION OF NANOBODY TARGETING DENGUE VIRUS NS1 PROTEIN

CROSS-REFERENCE TO RELATED APPLICATION

This application claims the priority benefit of China application no. 202311678044.5 filed on Dec. 8, 2023. The entirety of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Nov. 14, 2024, is named 151155_SEQUENCELISTING and is 3,330 bytes in size.

BACKGROUND OF THE INVENTION

Technical Field

The present disclosure relates to the technical field of biotechnology, and particularly relates to a preparation method and application of a nanobody targeting dengue virus NS1 protein.

Background of Related Art

Dengue fever is an acute infectious disease caused by dengue virus, which is transmitted to humans by mosquitoes such as *Aedes*. Clinical manifestations include asymptomatic flu-like symptoms, and severe conditions due to increased vascular permeability caused by fluid loss and organ dysfunction, which are lethal. Dengue fever has indeed become a significant global health concern. The World Health Organization reported 5.2 million cases of dengue virus infection alone in 2019. In recent years, an estimated 3.9 billion people in 129 countries and regions are at risk of infection. Dengue fever has become a major severe disease in Asian and Latin American countries, with a high mortality rate. The mortality rate among hospitalized patients can reach up to 10% in underdeveloped areas. Therefore, rapid diagnosis of dengue fever is crucial for clinical treatment and pathological research.

The dengue virus is a member of the genus Flavivirus in the family Flaviviridae, and consists of four serotypes. The dengue virus has an icosahedral symmetric envelope structure containing a single-stranded genome of positive polarity. Dengue non-structural protein (NS1) is highly conserved protein in the dengue virus, with a size of 48-50 kDa. NS1 is translated from the viral RNA as part of a polypeptide, and further forms NS1 dimers. In a human body, the NS1 protein in the form of dimers further assembles into multimers and is released into blood. Therefore, NS1 has become one of the important diagnostic markers for dengue fever. In addition, NS1 has been proven to play a significant role in the pathogenicity of the virus. A study has also shown that severe dengue disease is closely associated with high levels of circulating NS1 in the plasma of dengue-infected patients (Lim P-Y, Ramapraba A, Loy T, Rouers A, Thein T-L, Leo Y-S, et al. (2023) *A Nonstructural Protein* 1 *Capture Enzyme-linked Immunosorbent Assay Specific for Dengue Viruses. PLoS ONE* 18 (5): e0285878).

Traditional diagnostic methods for dengue fever, such as viral RNA detection, have the disadvantages of complex operation, time-consuming process and high cost, therefore, there is an urgent need for a faster and more sensitive means as a pre-diagnosis method of dengue fever. At present, commercial enzyme-linked immunosorbent assay kits are available for detecting NS1 protein in the blood. However, as a common detection element of immunoassay, traditional monoclonal antibodies have deficiencies such as high cost, poor stability, and difficulty in large-scale production, which limit the sensitivity and accuracy of immunoassay. Therefore, it is necessary to develop a highly sensitive and specific recognition element to replace the monoclonal antibodies. A nanobody is a protein fragment with a size about 15 kDa extracted from a heavy-chain camel antibody and is a smallest known structure capable of being specifically binding to antigens at present. Nanobodies usually exhibit excellent thermal stability and conformational stability. Therefore, a nanobodies-based immunoassay is very suitable for pathogen detection. In addition, the nanobody can be expressed in large quantities, is low in preparation cost, exhibits strong specific target recognition ability, and has high sensitivity, proving enormous application potential in the field of rapid diagnosis and treatment of diseases.

SUMMARY OF THE INVENTION

Based on the research background above, in order to overcome the deficiencies of traditional monoclonal antibodies, the present disclosure aims to develop a highly sensitive and specific nanobody to replace the traditional monoclonal antibodies, and applies the nanobody to various dengue virus detection and analysis platforms.

In a first aspect, the present disclosure provides a nanobody targeting dengue virus NS1 protein, where the nanobody is a VHH antibody having an amino acid sequence shown in SEQ ID NO: 1. The nanobody exhibits excellent binding affinity and specificity with the dengue virus NS1 protein.

Further, the VHH antibody has a nucleotide sequence shown in SEQ ID NO: 2.

In a second aspect, the present disclosure provides a preparation method of the nanobody targeting dengue virus NS1 protein, and the method includes:

(1) transforming dengue virus NS1 protein expression plasmid into *Escherichia coli* BL21(DE3) cells; after culturing to a logarithmic growth phase, using isopropyl-β-D-thiogalactoside (IPTG) to induce the expression of engineering bacteria, purifying the expressed dengue virus NS1 protein by using a Ni-NAT gravity column to obtain high-purity protein, and identifying the dengue virus NS1 protein by using sodium dodecyl sulfate polyacrylamide gel electrophoresis (SDS-PAGE) and enzyme-linked immunosorbent assay (ELISA);

(2) extracting lymphocytes from a non-immunized alpaca, and extracting a total RNA, synthesizing cDNA and using PCR to amplify a fragment encoding a VHH gene fragment; after digestion with a fast digestion, ligating the fragment into phagemid pComb3XSS using T4 ligase, introducing recombinant phagemid into *Escherichia coli* TG1 to construct a nanobody phage library, which has an estimated capacity of about $2\times10^{10}$ with low sequence redundancy and good diversity;

(3) coating the expressed dengue virus NS1 protein onto enzyme-linked immunosorbent assay wells, incubating for a period of time after inputting a recombinant phage, washing with PBST to remove the non-specifically bound recombinant phage, eluting with acid the specifically bound phage, amplifying the eluted phage, and determining a titer for a next round of panning or analysis; and performing 3-5 rounds of panning according to the steps of "adsorption-washing-elution-amplification", and carrying out panning progressively by changing conditions, such as a PBST concentration, and phage incubation time, to screen out the nanobody phage with higher affinity and stronger specificity; and (4) after several rounds of screening, randomly selecting 20 phages for Phage-ELISA identification, using dengue virus NS1 protein, bovine serum albumin and ovalbumin as negative controls and PBS as blank controls; obtaining three recombinant phage-displayed nanobodies with good specific binding to the dengue virus NS1 protein, and amplifying the three phage-displayed nanobodies, extracting plasmids thereof and sequencing to obtain a nanobody.

Further, the dengue virus NS1 protein in the present disclosure is produced via a prokaryotic expression system, and a pH value of an elution method ranges from 2 to 10.

Further, a construction method of a phage-displayed nanobody library is the present disclosure includes the following steps:

(1) amplifying the gene fragment encoding the nanobody from alpaca lymphocytes, introducing Sfi I restriction sites at both ends of the nanobody; and (2) ligating the fragment into phagemid pComb3XSS and using T4 ligase to construct the phage-displayed library.

Further, a pH elution screening method includes the following steps:

(1) coating 2.5-30 μg/mL of dengue virus NS1 protein onto 400 μL enzyme-linked immunosorbent assay wells at 4° C. for 10-14 h;

(2) washing the plate 5-10 times with 0.05-0.25% PBST, and blocking with bovine serum albumin (BSA) or ovalbumin (OVA) at 37° C. for 1-2 h;

(3) washing the plate 5-10 times with 0.05-0.25% PBST, adding $2 \times 10^{10}$ recombinant phage and incubating at 37° C. for 60-120 min; and (4) washing the plate 5-10 times with 0.05-0.25% PBST, adding 100-200 μL of 0.1M Gly-Hcl (pH 2.2) and incubating for 8-10 min, adding 30-45 μL of 1M Tris-Hcl (pH 9.1) to determine a titer, and picking monoclonal phages for Phage-ELISA identification.

Further, the recombinant phage is constructed by recombining the phagemid pComb3XSS with a helper phage M13K07.

In a third aspect, the present disclosure provides an application of the nanobody targeting dengue virus NS1 protein, the phage-displayed nanobody can specifically bind to the dengue virus NS1 protein, can be used as a substitute for traditional monoclonal antibodies targeting the dengue virus NS1 protein, and can be applied in the field of dengue fever immunoassay.

The present disclosure has the following beneficial effects:

(1) Compared with the traditional monoclonal antibodies, the phage-displayed nanobody in the present disclosure has the advantages of small size, high stability, simple preparation, low cost, and large-scale production capability.

(2) One nanobody sequence provided in the present disclosure is reported for the first time both at home and abroad, having great innovative achievements.

(3) The phage-displayed nanobody provided in the present disclosure can serve as core detection elements and be applied to various immunoassay platforms for detecting the dengue virus.

BRIEF DESCRIPTION OF THE DRAWINGS

FIGURE shows results of Phage-ELISA verification of affinity and specificity of 1-20 phage-displayed nanobodies; and a horizontal axis indicates phage clone numbers, and a vertical axis indicates an absorbance value at 450 nm.

DETAILED DESCRIPTION OF THE EMBODIMENTS

Material, reagents, and formulations used in the examples of the present disclosure are as follows:

Main Experimental Material:

Dengue virus NS1 protein plasmid, *Escherichia coli* BL21(DE3), *Escherichia coli* TG1, a helper phage M13K07, and a phagemid pComb3XSS stored in the laboratory.

Main Reagents:

Ovalbumin and bovine serum albumin purchased from USA Sigma-Aldrich; horseradish peroxidase (HRP) enzyme-conjugated anti-M13 monoclonal antibody purchased from Sino Biological, Inc.; skim milk powder, 3,3', 5,5'-tetramethylbenzidine (TMB) chromogenic solution, and isopropyl-β-D-thiogalactoside (IPTG) purchased from Sangon Biotech (Shanghai) Co., Ltd.; and LB broth, and 2×YT medium purchased from Qingdao Hi-Tech Industrial Park Hope Bio-Technology Co., Ltd.

Main Reagent Formulations:

1. 2×YT liquid medium: 31 g of 2×YT powder was weighed and dissolved in 1000 mL of ultrapure water and autoclaved at 121° C. for 15 min;

2. 2×YT solid medium: 31 g of 2×YT powder and 18 g of agar were weighed and dissolved in 1000 mL of ultrapure water and autoclaved at 121° C. for 15 min;

3. LB liquid medium: 25 g of LB medium was weighed and dissolved in 1000 mL of ultrapure water and autoclaved at 121° C. for 15 min;

4. 20% polyethylene glycol (PEG)-NaCl: 50 g of PEG-8000 and 36 g of NaCl were dissolved in ultrapure water by heating, then made up to a volume of 250 mL and autoclaved for 15 min;

5. Elution buffer: 0.2M glycine (Gly) was prepared, hydrochloric acid was added to adjust a pH value to 2.2, and then autoclaved for 15 min; and 6. Neutralization buffer: hydrochloric acid was added to 1M tris(hydroxymethyl)aminomethane to adjust a pH value to 9.1, and then autoclaved for 15 min.

I. Prokaryotic Expression of Dengue Virus NS1 Protein (1) BL21(DE3) containing a dengue virus NS1 protein plasmid was streaked on an LB plate and incubated at 37° C. for 12-14 h;

(2) a single colony was picked from the plate and inoculated into 5 mL of LB medium, then incubated at 37° C. for 12-14 h;

(3) 500 μL of bacterial solution was taken and inoculated into 50 mL of LB medium, incubated at 37° C. for 3 h, 0.1-0.5 M of IPTG was then added and incubated at 20° C. for 12-14 h;

(4) centrifugation was performed at 4000-8000 rpm for 10-20 min, bacterial pellet was taken and resuspended in PBS, and was then subjected to ultrasonic disruption at 200-300 W for 10-20 min; and (5) centrifugation was performed at 4000-8000 rpm for 10-20 min, supernatant was collected and purified by a Ni-NAT gravity column; and purity and activity of a purified product were identified by sodium dodecyl sulfate polyacrylamide gel electrophoresis (SDS-PAGE) and enzyme-linked immunosorbent assay (ELISA).

II. Construction of Natural Phage-Displayed Nanobody Library (1) peripheral blood lymphocytes were extracted from many alpacas;

(2) 1-2 mL of Trizol was added to the cells, 0.5-1 mL of isopropanol was added for inverting several times to mix evenly, and then placed at room temperature for 10-20 min;

(3) centrifugation was performed at 10,000-14,000 g for 10-20 min, and supernatant was discarded to obtain RNA pellet of the cells;

(4) 1-3 mL of 75% ethanol was added and inverted several times to mix evenly, and placed at room temperature for 10 min, centrifugation was performed at 10,000-14,000 g for 10-20 min, and supernatant was discarded;

(5) inversion at room temperature was performed for 5-10 min for drying or a vacuum dry was performed, 25-50 μL of DEPC-ddH$_2$O was added to dissolve the RNA, RNA quality was detected by using gel electrophoresis, and concentration thereof was determined. The extracted RNA was subjected to reverse transcription using a reverse transcription kit to obtain a cDNA template;

(6) a VHH fragment/pComb3XSS digestion: 1-5 g of VHH fragment/pComb3XSS, 20-140 μL of RNase-free H$_2$O, 1-2 μL of Sfi I fast digestion, 5-10 μL of fast digestion buffer, with reaction conditions of 37° C. for 45-60 min;

(7) a VHH fragment was cloned into phagemid pComb3XSS: 10-30 ng of a digested VHH fragment, 50-100 ng of pComb3XSS digestion, 0.8-1.2 μL of T4 ligase, 1-3 μL of T4 ligase buffer, and 7-14 μL of RNase free H$_2$O, with reaction conditions of 16° C. for 12-18 h;

(8) 100-200 ng of pComb3XSS—a VHH recombinant phagemid was transformed into competent *E. coli* TG1 and incubated at 37° C. for 10-14 h; and all single colonies were eluted from the plate to form a phage nanobody library;

(9) 50-100 μL of eluted phage library was taken and inoculated into 5 mL of 2×YT/ampicillin (Amp) medium, and cultured to a logarithmic growth phase, and a helper phage M13K07 was added at an inflection ratio of *E. coli*: phage=1:20, and then incubated at 37° C. for 1 h;

(10) 5 mL of the above culture system was totally added into 50 mL of 2×YT/Amp/Kanamycin (Kana) medium and incubated at 37° C. for 12 h;

(11) centrifugation was performed at 12,000-16,000 g for 10-15 min, supernatant was collected, 12 mL of PEG/NaCl was added to the supernatant to obtain a mixture, and the mixture was left on ice for 4-6 h;

(12) centrifugation was performed at 12,000-16,000 g for 30-40 min, supernatant was discarded, 1 mL of PBS was added to resuspend, 200-300 μL of PEG/NaCl was added to obtain a mixture, and the mixture was left on ice for 1-2 h; and

(13) centrifugation was performed at 12,000-16,000 g for 30-40 min, supernatant was discarded, 200-300 μL of PBS was added to resuspend, 10 μL of phage was taken to determine a recombinant phage titer, which could reach up to 2×10$^{10}$, and the phage was aliquoted for later screening.

III. Screening of the Phage-Displayed Nanobody Against Dengue Virus NS1 Protein (1) An ELISA plate was washed 3-5 times with sterile water in an ultra-clean workbench, and then sterilized under UV light for 60-75 min;

(2) dengue virus NS1 protein was diluted with PBS to a final concentration of 5-10 μg/mL, and the diluted dengue virus NS1 protein was added to the ELISA plate at 100-200 μL per well, and coated at 4° C. for 10-14 h;

(3) the plate was washed 5 times with PBS and then patted dry with sterile paper, and 250-350 μL of 1-3% BSA-PBS blocking solution was added to each well for blocking at 37° C. for 2 h;

(4) the plate was washed 5 times with PBS and then patted dry with sterile paper, and 2×10$^{10}$ recombinant phage library was taken and mixed with 150-200 μL of PBS, then added to the ELISA plate for binding at 37° C. for 60-120 min;

(5) the plate was washed 5 times with 0.1% PBST and then patted dry with sterile paper, 100 μL of Gly-HCl buffer was added and incubated at 37° C. for 8-10 min, an eluted product was aspirated, and 30-45 μL of Tris-HCl buffer was added quickly; and (6) 10 μL of phage was taken for gradient dilution, an eluted phage titer was determined, a panning recovery rate was calculated, the remaining phage was amplified and purified for a next round of screening or analysis; and the amplification steps are the same as those for construction of the phage-displayed nanobody library against dengue virus NS1 protein; and (7) the steps (1) to (6) were a first round of amplification, and a panning steps for second to fifth rounds were basically the same, an amount of phage input for each round was 2×10$^{10}$ pfu per well, a coating concentration of the dengue virus NS1 protein was decreased from 30 μg/mL down to 2.5 μg/mL round by round, 1-3% OVA-PBS and 1-3% BSA-PBS blocking solutions were used for alternating blocking, a binding time of the phage input and the dengue virus NS1 protein were reduced from 120 min to 30 min round by round, and an elution buffer concentration ranged from 0.05% to 0.25% PBST. The panning scheme was shown in Table 1.

TABLE 1

Screening of the phage-displayed nanobody against dengue virus NS1 protein

| Round | NP protein coating concentration | Blocking solution | Phage volume | Elution buffer | Incubation time |
|---|---|---|---|---|---|
| I | 30 | BSA-PBS | 2 × 10$^{10}$ | 0.05% PBST | 120 min |
| II | 15 | OVA-PBS | 2 × 10$^{10}$ | 0.05% PBST | 90 min |
| III | 10 | BSA-PBS | 2 × 10$^{10}$ | 0.1% PBST | 60 min |
| IV | 5 | OVA-PBS | 2 × 10$^{10}$ | 0.25% PBST | 45 min |
| V | 2.5 | BSA-PBS | 2 × 10$^{10}$ | 0.25% PBST | 30 min |

III. Screening and Identification of Specific Phage Clone

After five rounds of screening were completed, single colonies of 20 phage-displayed nanobodies were selected for amplification and identification by Phage-ELISA. The specific steps were as follows:

(1) 20 single colony clones were picked and inoculated into 1 mL of 2×YT/Amp liquid medium and cultured at 37° C., 220 rpm for 12-14 h;

(2) 100-150 µL of the above culture was taken and added to 1 mL of 2×YT/Amp liquid medium, mixed thoroughly and shaken at 220 rpm for 2-3 h until a logarithmic growth phase;

(3) the helper phage M13K07 was added to each tube at a ratio of cell:phage=1:1, and incubated at 37° C. for 15-20 min, and cultured by shaking at 220 rpm for 30-45 min by shaking;

(4) centrifugation was performed at 4° C. at 8000-10000 rpm for 2-5 min, 1-1.5 mL of 2×YT/Amp/Kana was added to resuspend, and cultured by shaking at 37° C. at 250 rpm for 10-14 h;

(5) after the incubation, centrifugation was performed 8,000-10,000 rpm for 10-12 min, supernatant was aspirated and transferred into a sterile centrifuge tube, labeled and marked, and then stored at 4° C. for ELISA identification;

(6) 100-200 µL of dengue virus NS1 protein, bovine serum albumin and ovalbumin with a concentration of 1-5 µg/mL were taken from each well, and coated onto the ELISA plate at 4° C. for 10-14 h;

(7) the coating solution was discarded, the plate was washed three times with 0.05% PBST, and 250-350 µL of 3-5% skim milk powder was added to each well and incubated at 37° C. for 2-3 h;

(8) the plate was washed three times with 0.05% PBST, and 100 µL of the panned phage supernatant culture was added to each well coated with the dengue virus NS1 protein, bovine serum albumin and ovalbumin, and then incubated at 37° C. for 45-60 min;

(9) the plate was washed six times with 0.05% PBST, 100-200 µL of anti-M13 secondary antibody was added to each well and incubated at 37° C. for 45-60 min;

(10) the plate was washed seven times with 0.05% PBST, 100 µL of TMB chromogenic solution was added and incubated at 37° C. for 10-15 min, 50 µL of 1M $H_2SO_4$ was added to each well, and an absorbance at a wavelength of 450 nm (A450 nm) was measured. FIGURE shows binding capability of the selected 20 recombinant phage clones with the dengue virus NS1 protein, bovine serum albumin (BSA) and ovalbumin (OVA). A horizontal axis indicates phage clone numbers, and a vertical axis indicates a absorbance value at 450 nm; and

(11) among the 20 selected clones, all of the 20 clones were able to bind to the dengue virus NS1 protein; where clones Nb3, Nb10, and Nb18 exhibited strong binding capability and specificity with the dengue virus NS1 protein, the three clones were amplified and sequenced using designed primers, and one phage-displayed nanobody amino acid sequences with different sequences was obtained through analysis.

Specific application of the present disclosure: the present disclosure particularly relates to a phage-displayed nanobody capable of binding to the dengue virus NS1 protein, which can express a nanobody corresponding to the amino acid via in vitro protein expression technology, and can be utilized as a detection element for dengue fever in analytical systems such as enzyme-linked immunosorbent assay, immunochromatography test strip and immunosensor, and the development of detection kits.

The above examples describe the implementation methods of the present disclosure.

Those skilled in the art may make various applications and improvements without departing from the spirit of the present disclosure, all of which fall within the scope of protection of the present disclosure.

---

What is claimed is:

1. A nanobody targeting dengue virus NS1 protein, wherein the nanobody is a VHH antibody, and the nanobody has the amino acid sequence shown in SEQ ID NO: 1.

2. A nucleic acid encoding the nanobody targeting dengue virus NS1 protein according to claim 1, wherein the nucleotide sequence of the nucleic acid is shown in SEQ ID NO: 2.

3. A dengue virus detection kit, comprising the nanobody targeting dengue virus NS1 protein according to claim 1.

* * * * *